United States Patent [19]

Stevanato

[11] Patent Number: 4,713,062
[45] Date of Patent: Dec. 15, 1987

[54] READY TO USE SYRINGE

[75] Inventor: Giovanni Stevanato, Chiasso, Switzerland

[73] Assignee: Vecta Glass Company Ltd., London, England

[21] Appl. No.: 868,076

[22] Filed: May 29, 1986

[30] Foreign Application Priority Data

May 29, 1985 [LU] Luxembourg ............................ 85916

[51] Int. Cl.⁴ .............................................. A61M 5/24
[52] U.S. Cl. ...................................................... 604/203
[58] Field of Search ...................................... 604/86-91, 604/187, 201-206, 218

[56] References Cited

U.S. PATENT DOCUMENTS 399,296 11/1976 Cloyd .
2,549,417 4/1951 Brown .
2,576,951 12/1951 Lockhart ......................... 604/203 X
3,980,083 9/1976 Elliott .............................. 604/203 X
4,226,236 10/1980 Genese .................................. 604/89

FOREIGN PATENT DOCUMENTS 2003286 11/1969 France .
1256522 12/1967 United Kingdom .

Primary Examiner—John D. Yasko
Attorney, Agent, or Firm—Charles E. Brown; Charles A. Brown

[57] ABSTRACT

The invention provides a ready to use syringe easy to use, of low cost and rapid packing, having high security against bacterial pollution, comprising a cylindrical shaped container for the injectable solution also serving as piston and being closed by a piston plug, which may be perforated by a point extending downwardly from a small suction tube, fixed to the outer casing of the syringe in correspondance with the head for connection to the guide cone of the administration needle.

10 Claims, 7 Drawing Figures

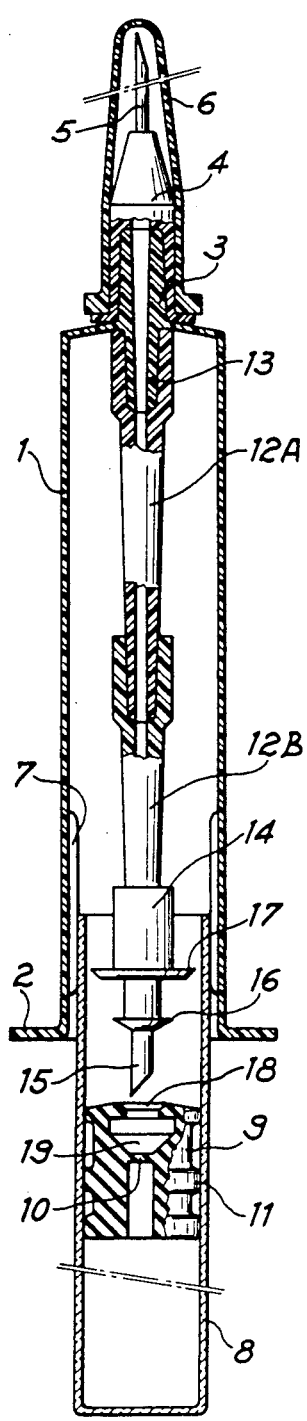
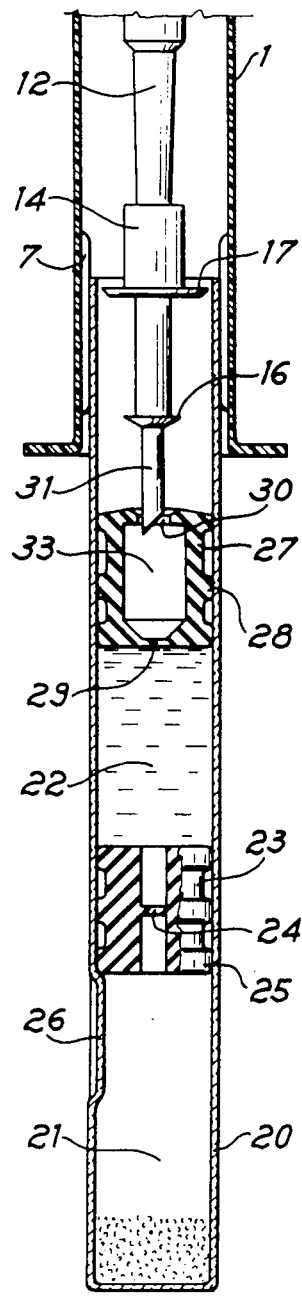
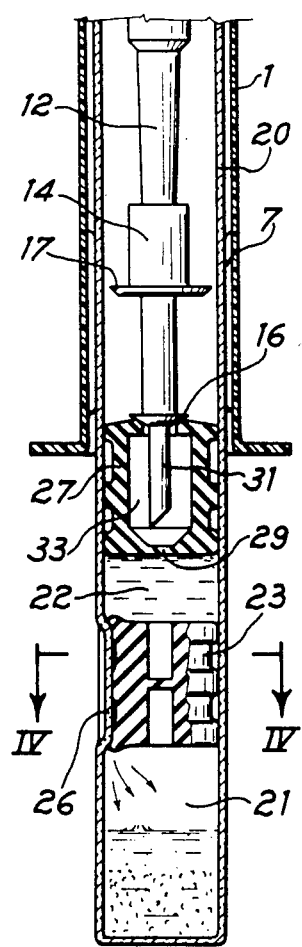
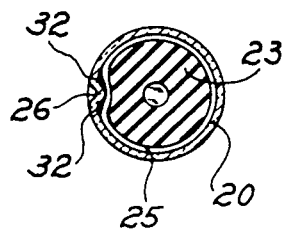

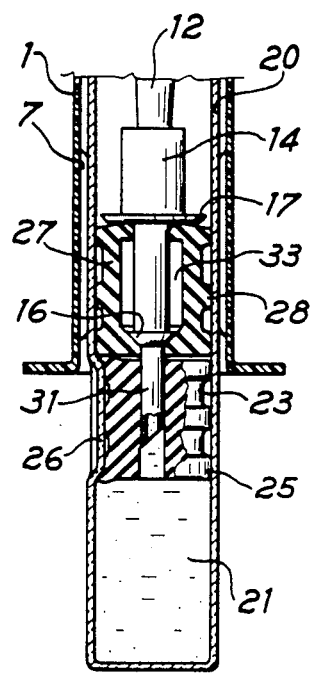
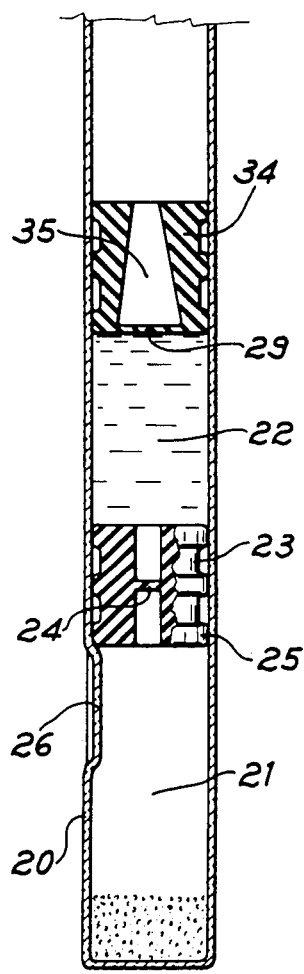
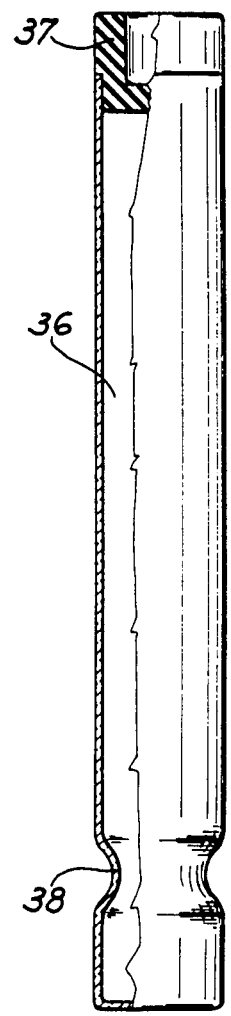

READY TO USE SYRINGE

BACKGROUND OF THE INVENTION

The present invention relates to a ready to use syringe which has numerous advantages with respect to ready to use syringes existing at the present time, which have a complex structure and a high production cost.

By the term ready to use syringe is meant a syringe in which the injectable solution has already been introduced during the packing phase, and which may be preferably contained in a sterile protective case.

The ready to use syringe of the present invention not only overcomes the above mentioned drawbacks, thus resulting in a simplified structure easy to use and of a lower cost, it also greatly reduces the possibility of bacterial pollution of the injectable solution, since this latter is only in contact with a sterile material plug piston, apart of course from the walls of the sterilized glass container.

SUMMARY OF THE INVENTION

The ready to use syringe of the present invention is characterized by the fact that it comprises, in combination, a cylindrical shaped container for the injectable solution also acting as piston and closed by a piston plug, which may be perforated by a point extended downwardly from a small suction tube, fixed to the outer casing of the syringe in correspondence with the head connecting to the leading cone of the administration needle.

In a variant of the present invention, the container may be used as ready to use ampoule for medicaments formed from two components to be mixed at the time of use. In this case, the container has a second inner plug which divides the container into two chambers, each containing a component, which are brought together at the time of use, comprising this inner plug disposed so as to be in correspondance with an inner projection of the wall of the container which deforms the inner plug, thus creating a communication passage between the two chambers of the container which allows the components to be mixed.

Further characteristics of the syringe of the present invention consist of means for fixing the small suction tube to the piston plug with the possibility of movement for controlling the correct execution of the injection, in an appropriate container for taking samples of body fluids for analysis, as well as the provision of inner members for guiding the sliding of the injectionable solution container in the outer casing of the syringe.

BRIEF DESCRIPTION OF THE DRAWINGS

These aims and other features and advantages of the ready to use syringe of the present invention will be clearer and more evident from reading the following detailed description of some preferred embodiments, which are however given solely by way of example and in no wise limitative of the scope of the invention, with reference to the accompanying drawings in which:

FIG. 1 is a complete sectional view of the ready to use syringe of the present invention in its most general embodiment for medicaments comprising a single component;

FIG. 2 is a similar partial view of the embodiment for medicaments having two components, before use;

FIG. 3 is a view similar to FIG. 2, but showing the phase of mixing the two components;

FIG. 4 is a cross section through the line IV—IV of FIG. 3, showing the small channels through which the component passes from the upper chamber to the lower chamber;

FIG. 5 is a view similar to FIGS. 2 and 3 but showing the final preparation phase for the injection;

FIG. 6 is a view similar to the preceding one, showing a different embodiment of the outer plug of the container for a two component medicament and FIG. 7 is a complete view in partial section, particularly designed for taking samples of body fluids for analysis, to be used with a ready to use syringe of the present invention.

Referring now first of all to FIG. 1 of the accompanying drawings, the complete structure of the ready to use syringe of the present invention is shown in its most general form, that is to say the one with an ampoule for a single component medicament. The syringe has then an external casing 1, which ends at the bottom in the usual annular projecting edge 2 and at the top by a head 3 for connection to the zone 4 guiding the administration needle 5, protected by the relative needle protective cap 6, the whole being made from an appropriate plastic material.

In the vicinity of the lower open mouth, the inner surface of the outer casing 1 has projection 7 which serves as a guide for the cylindrical container or ampoule 8 for the injectable solution, generally made from glass, which is closed by a plug 9, preferably made from F.U. rubber or another appropriate material, which has a central dividing wall 10 which is perforated at the time of use, and external annular projections 11 for perfect sealing against the inner wall of container 8. Although the position of the annular sealing projections 11 on the outer surface of plug 9, as well as the position of the dividing wall or central membrane 10 could be different from those shown in the drawings, the assymmetrical position of these elements has been chosen for facilitating removal of the plug from the mold, thus allowing a substantially higher molding rate and consequently an improved economy of production of the part.

For taking the liquid from inside the container or ampoule 8 and feeding it to the administration needle 5, a small suction tube is provided formed of a certain number of slightly tapered modular elements 12 which fit into one another. The upper module 12A fits onto a tube 13 forming part of the head 3 of the body 1 of the syringe, whereas the lower module 12B fits into the base 14 of a perforating point 15, having a small collar 16 and a stop ring 17. The ring provides sealing with the glass container so as to guarantee protection of the outer part of the piston and the point of the perforator which must remain sterile. Several sealing rings may also be provided. The small suction tube may also be formed as a single element of appropriate length.

When the syringe is to be used, by pushing the cylindrical container or ampoule 8 from the top, which thus also acts as a piston for the syringe, point 15 will pass through the upper open hole 18 of plug 9 and will perforate the central dividing wall 10, and will no longer be able to be detached from plug 9, since collar 16, which will then be in cavity 19 formed in plug 9 between the central wall 10 and the upper wall 18, can no longer leave this latter because of its truncated cone shape which allows it to enter but not to leave. However, cavity 19 allows point 15 to accomplish a limited movement determined by the size of cavity 19 and by the distance between collar 16 and sealing ring 17, thus allowing the usual visual check to be made when making an injection to check by means of a slight suction if the needle has been correctly introduced into the body tissues of the patient.

Referring now to FIGS. 2 to 5, the embodiment of the syringe of the present invention is shown with respect to an ampoule for two-component medicaments, which may be either a medicinal powder to be dissolved at the time of use with the solvent liquid, or two liquids to be mixed together solely at the time of use.

Consequently, in this case, the ampoule or cylindrical container 20 is subdivided into two chambers, the lower chamber 21 containing the medicinal powder or the first liquid and the upper chamber 22 containing the solvent or the second liquid. The lower chamber 21 is closed by a plug 23 having a central dividing wall 24 and external sealing rings 25, placed immediately above an inner projection or indentation 26, obtained in the glass wall of the ampoule from the outside towards the inside, whereas the upper chamber 22 is closed by a plug 17 also having external sealing rings 28, but in which the perforable dividing wall 29 coincides with the bottom of the plug, whose top has an open mouth 30.

In this case, the perforating point 31 is substantially longer than point 15 of the embodiment shown in FIG. 1 and the distance between collar 16 and stop ring 17 is greater, for reasons which will be explained hereafter. It should also be mentioned that the small suction tube may be formed of more than two modular elements 22, depending on the length of the syringe, determined as usual by the volume of solution to be injected (1 cc, 2 cc, 5 cc, 10 cc, etc).

In FIG. 3 it can be seen how, by pushing the container or ampoule 20 upwardly, collar 16 comes to bear on the top of the upper plug 27 which is then pushed downwardly, acting as a piston and exerting a pressure on the liquid contained in the upper chamber 22, which pressure is transferred to the lower plug 23, which is then forced to move down until it is engaged against the indentation or projection 26, which, by crushing plug 23, opens a communication passage between the two chambers through the small channels 32 which are formed at the two sides of projection 26, this is why the liquid contained in the upper chamber 22 is transferred to the lower chamber 21 and mixes with the powder to be solubilized or the second liquid which is contained therein, whereas the air which is in the lower chamber 21 is transferred above the lower plug 23, and this operation may be effected in one or more steps.

After finishing the mixing and continuing to push the ampoule or container 20, the final position illustrated in FIG. 5 is reached where the perforating point 31 pierces first of all the bottom wall 29 of the upper plug 27, which will abut against the lower plug 23, and consequently the perforating point 31 will penetrate in this latter and also pierce its central dividing wall 24, thus allowing the solution to be taken for making the injection, and hereagain the inner cavity 33 of the upper plug 27 allows the needle to be slightly withdrawn for checking the correct introduction thereof into the body of the patient, without perforating point 31 being able to become detached, for it is prevented by collar 16 as in the embodiment shown in FIG. 1. The same result could in any case be obtained with a slightly different upper plug 34, shown in FIG. 6, where its inner cavity 35 is in the form of a truncated cone open at the top: even in this case, collar 16 would prevent the perforating point 31 from coming out, since it is considerably larger than the mouth of the inner cavity 35 and in addition widened out in the opposite direction.

It should be mentioned that in the ready to use syringes existing at present, when a two stage ampoule is provided for two components, it has a protuberance or impression projecting outwardly, which results in considerable disadvantages not only during production but also during use. The solution of the present invertion, with the inwardly projecting protuberance or impression of the ampoule, allows the container on the contrary to be treated as a cylindrical body without external protuberances which limit the possibilities thereof during work on automatic machines and does not allow ready labelling or stamping, and thus the production times and costs, even of this element of the syringe, drop considerably. It should also be mentioned that in this ampoule or container for two components, the powder to be solubilized may also be obtained by liophilizing the medicament directly in the container, instead of being introduced into a controlled amount of solution as before.

Finally, in FIG. 7 a cylindrical container 36 has been shown to be used as a piston with the syringe of the present invention, when it is desired to take samples of body fluids for analysis, and in this case the container has simply a small closure plug 37 and the lower annular groove 38 for easy handling.

From the foregoing it follows then that the ready to use syringe of the present invention fully complies with all the above mentioned aims, and numerous variants, modifications, additions and/or substitutions may be made thereto without for all that departing from the scope and spirit of the present invention, which are defined in the accompanying claims.

What is claimed is:

1. A ready to use syringe, said syringe comprising in combination a cylindrical shaped container for an injectable solution, said cylindrical shaped container also serving as a piston and being closed by a piston plug, said piston plug may be perforated by a point extending downwards from a small suction tube, said small suction tube being fixed to the outer casing of said syringe in correspondence with a head for recording to a guide cone of an administration needle, said point for perforating said piston plug being provided with means for securing the piston itself, preventing mutual detachment at the time of use, and allowing the visual control, by means of a slight suction resulting from the correct introduction of the administration needle into the tissue of a patient.

2. The ready to use syringe as claimed in claim 1, wherein said small suction tube is formed by modular element having a central through hole, which may be fitted together in a number determined by the length of the body of the syringe, to the lowest element of which the point for perforating the piston plug is fixed.

3. The ready to use syringe as claimed in claim 1, wherein said small suction tube may also be formed by a single element of adequate length.

4. The ready to use syringe as claimed in claim 1, wherein the piston plug of the container for the injectable solution has external annular protuberances for sealing and guiding on the inner wall of this container.

5. The ready to use syringe as claimed in claim 4, wherein the piston plug is pierced centrally in correspondance with a dividing wall or closure head.

6. The ready to use syringe as claimed in claim 1, wherein said means provided on the perforating point for securing the piston are formed by a collar in the form of a truncated cone shapedreel, which is fitted into an inner cavity of the piston plug, but cannot then be removed from its mouth, allowing only a movement equal to about the length of this cavity.

7. The ready to use syringe as claimed in claim 1, wherein the external body or casing of the syringe has on its inner wall guide projections for sliding therein of the container or ampoule for the injectable solution.

8. The ready to use syringe as claimed in claim 1, wherein, for using it as an ampoule for medicaments formed of two components to be mixed together at the time of use, the cylindrical container has a second inner plug which divides the container into two chambers, each chamber containing a component, which are brought together at the time of use, the inner plug being disposed so as to be in correspondence with an inner projection or impression of the wall of the container, which deforms the inner plug and creates a communication passage between the two chambers of the container, thus allowing mixing of said components.

9. The ready to use syringe as claimed in claim 8, wherein the perforating point of said modular suction tube, after mixing of the two components, is adapted for perforating the two plugs now engaged with each other, for taking the ready to use solution, the movement of these plugs in the container or ampoule being provided by the pressure exerted by the collar of the small modular tube, as the container or ampoule is pushed into the syringe.

10. The ready to use syringe as claimed in the preceding claims, also comprising a cylindrical container for taking samples of body fluids, having a closure plug adapted for handling.

* * * * *